(12) United States Patent
Fujikane et al.

(10) Patent No.: US 9,593,030 B2
(45) Date of Patent: Mar. 14, 2017

(54) LIQUID TREATMENT APPARATUS AND LIQUID TREATMENT METHOD

(71) Applicant: Panasonic Intellectual Property Management Co., Ltd., Osaka (JP)

(72) Inventors: Masaki Fujikane, Osaka (JP); Mari Onodera, Osaka (JP); Shin-ichi Imai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/693,896

(22) Filed: Apr. 23, 2015

(65) Prior Publication Data

US 2015/0225264 A1    Aug. 13, 2015

Related U.S. Application Data

(63) Continuation of application No. PCT/JP2014/003898, filed on Jul. 24, 2014.

(30) Foreign Application Priority Data

Nov. 18, 2013   (JP) .................................. 2013-238037

(51) Int. Cl.
*C02F 1/46* (2006.01)
*C02F 1/50* (2006.01)
(Continued)

(52) U.S. Cl.
CPC .............. *C02F 1/4608* (2013.01); *A61L 2/14* (2013.01); *A62D 3/19* (2013.01); *C02F 1/50* (2013.01);
(Continued)

(58) Field of Classification Search
CPC ............. B01D 21/283; B01L 3/502753; B01L 3/502761; B01L 2400/0436;
(Continued)

(56) References Cited

U.S. PATENT DOCUMENTS 5,630,915 A     5/1997  Greene et al.
5,766,447 A *   6/1998  Creijghton ................ A61L 2/02
                                                                204/164
(Continued)

FOREIGN PATENT DOCUMENTS

EP          2692694      2/2014
JP          9-507428     7/1997
(Continued)

OTHER PUBLICATIONS

International Search Report of PCT application No. PCT/JP2014/003898 dated Sep. 2, 2014.
(Continued)

*Primary Examiner* — Walter D Griffin
*Assistant Examiner* — Cameron Allen
(74) *Attorney, Agent, or Firm* — McDermott Will & Emery LLP (57) ABSTRACT

A liquid treatment apparatus includes a dielectric tube through which water to be treated flows, a first electrode at least a part of which is disposed in the dielectric tube, a second electrode at least a part of which is disposed in the dielectric tube at a position upstream of the first electrode, a gas supplier operative to generate a bubble by supplying a gas into the water to be treated, and a power supply operative to apply a voltage between the first electrode and the second electrode in a state in which the bubble covers a conductor-exposed portion of the first electrode.

15 Claims, 4 Drawing Sheets

(51) Int. Cl.
    *C02F 1/72*         (2006.01)
    *A62D 3/19*        (2007.01)
    *A61L 2/14*        (2006.01)
    *H05H 1/24*       (2006.01)
    *H05H 1/46*       (2006.01)

(52) U.S. Cl.
    CPC ............. *C02F 1/72* (2013.01); *H05H 1/2406* (2013.01); *C02F 2201/003* (2013.01); *C02F 2201/4619* (2013.01); *C02F 2201/46175* (2013.01); *C02F 2201/48* (2013.01); *C02F 2303/04* (2013.01); *C02F 2305/023* (2013.01); *C02F 2307/12* (2013.01); *H05H 2001/245* (2013.01); *H05H 2001/4697* (2013.01); *H05H 2245/1225* (2013.01)

(58) Field of Classification Search
    CPC ..... B01L 2200/0652; B01L 2300/0816; B01L 2200/0636; B01L 2200/10; B01L 2300/0864; G01N 33/5044; G01N 2015/142; G01N 33/5005; G01N 33/05; C02F 1/46
    See application file for complete search history.

(56) References Cited

U.S. PATENT DOCUMENTS

| | | | |
|---|---|---|---|
| 6,390,638 | B1 * | 5/2002 | Miller .................. G02B 6/0055 362/23.13 |
| 2004/0007539 | A1 * | 1/2004 | Denes .................. C02F 1/4608 210/748.18 |

FOREIGN PATENT DOCUMENTS

| | | |
|---|---|---|
| JP | 2000-093967 | 4/2000 |
| JP | 2007-207540 | 8/2007 |
| JP | 2009-255027 | 11/2009 |
| JP | 2013-150975 | 8/2013 |
| WO | 95/18768 | 7/1995 |
| WO | 99/47230 | 9/1999 |
| WO | 2008/123749 | 10/2008 |
| WO | 2012/134350 | 10/2012 |

OTHER PUBLICATIONS

The Extended European Search Report dated Oct. 6, 2016 for the related European Patent Application No. 14854888.6.

\* cited by examiner

LIQUID TREATMENT APPARATUS AND LIQUID TREATMENT METHOD

BACKGROUND

1. Technical Field

The present disclosure relates to a liquid treatment apparatus and a liquid treatment method.

2. Description of the Related Art

Sterilizing apparatuses have been proposed that treat water to be treated, such as contaminated water, with plasma. For example, Japanese Patent No. 4784624 describes a sterilizing apparatus including a high-voltage electrode and a ground electrode that are disposed with a predetermined space therebetween in water to be treated within a treatment tank. The sterilizing apparatus, having such a structure, causes an electrical discharge by applying a high-voltage pulse to these electrodes, to generate plasma in a bubble that is formed by instantaneous boiling, thereby generating OH, H, O, $O_2^-$, $O^-$, and $H_2O_2$, which kills microorganisms and bacteria.

SUMMARY

Existing apparatuses have a problem of low efficiency when treating a liquid.

One non-limiting and exemplary embodiment provides a liquid treatment apparatus and a liquid treatment method for efficiently treating a liquid.

A liquid treatment apparatus according to an aspect of the present disclosure includes: a dielectric tube through which water to be treated flows, a first electrode at least a part of which is disposed in the dielectric tube, a second electrode at least a part of which is disposed in the dielectric tube at a position upstream of the first electrode, a gas supplier operative to generate a bubble by supplying a gas into the water to be treated, and a power supply operative to apply a voltage between the first electrode and the second electrode in a state in which the bubble covers a conductor-exposed portion of the first electrode.

The liquid treatment apparatus and the liquid treatment method according to the present disclosure enables a liquid to be efficiently treated.

It should be noted that comprehensive or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Overview of Embodiments

A liquid treatment apparatus according to an aspect of the present disclosure includes a dielectric tube through which water to be treated flows, a first electrode at least a part of which is disposed in the dielectric tube, a second electrode at least a part of which is disposed in the dielectric tube at a position upstream of the first electrode, a gas supplier that supplies a gas into the water to be treated and generates a bubble, and a power supply that applies a voltage between the first electrode and the at least a part of the second electrode that is located upstream of the first electrode in a state in which the bubble covers a conductor-exposed portion of the first electrode.

With such a structure, the liquid treatment apparatus according to the present disclosure can improve the efficiency when treating a liquid, i.e., water to be treated, and can treat the liquid in a short time. The liquid treatment apparatus according the present disclosure, which treats the liquid by using the dielectric tube, can realize reduction in the size of the apparatus.

In the present disclosure, the term "water to be treated" refers to a liquid to be treated by the liquid treatment apparatus. Typically, water to be treated includes bacteria and/or chemical substances, such as organic substances. However, water to be treated is not limited to a liquid that includes bacteria and/or chemical substances. In other words, in the present disclosure, the phrase "treating a liquid" refers not only to killing bacteria in a liquid and decomposing chemical substances in the liquid but also to, for example, generating radicals in a liquid that does not include bacteria and chemical substances.

In the liquid treatment apparatus according to an aspect of the present disclosure, for example, a longitudinal direction of the first electrode may cross, in the dielectric tube, a direction in which the water to be treated flows from the second electrode toward the first electrode.

In this case, the liquid treatment apparatus can suppress the stationary state of a bubble generated near the first electrode due to the flow of water to be treated from upstream. Thus, it is possible to improve the efficiency when treating a liquid and reduce the time required for treating the liquid.

In the liquid treatment apparatus according to an aspect of the present disclosure, for example, the power supply may apply the voltage in a state in which the bubble covers the conductor-exposed portion of the first electrode and the bubble is not in contact with the second electrode.

In this case, the liquid treatment apparatus according to the present disclosure can stably cause an electrical discharge and stably generate plasma.

In the liquid treatment apparatus according to an aspect of the present disclosure, for example, the power supply may cause an electrical discharge in the bubble and generate plasma by applying the voltage between the first electrode and the second electrode.

With such a structure, the liquid treatment apparatus can generate plasma in the bubble, which covers the conductor-exposed portion of the first electrode, and can generate radicals efficiently. Accordingly, the liquid treatment apparatus can treat a liquid in a short time.

In the liquid treatment apparatus according to an aspect of the present disclosure, for example, the dielectric tube may define a flow path through which the water to be treated flows from the second electrode toward the first electrode and through which the water to be treated and the bubble flow downstream from the first electrode.

In this case, radicals generated near the first electrode can contact the water to be treated in a region downstream of the first electrode. Thus, it is possible to improve the efficiency when treating a liquid and reduce the time required for treating the liquid.

The liquid treatment apparatus according an aspect of the present disclosure, for example, may further include an insulator disposed in the dielectric tube so as to form a space around the first electrode, the insulator having an opening through which the space is connected to the dielectric tube, and the gas supplier may generate the bubble in the water to be treated from the opening in the insulator by supplying the gas to the space.

With such a structure, the liquid treatment apparatus can easily create a state in which the first electrode is covered by the bubble. By generating plasma in this state, the liquid treatment apparatus can generate radicals efficiently. Accordingly, it is possible to treat a liquid in a short time.

In the liquid treatment apparatus according to an aspect of the present disclosure, for example, the first electrode may include a metal electrode portion disposed in the dielectric tube and a metal fastener that fixes the first electrode in place and that is connected to the power supply, and the metal electrode portion and the metal fastener may be made of different materials.

With such a structure, in the liquid treatment apparatus, for example, a metal material that is highly resistant to plasma can be used for the metal electrode portion, and a metal material that can be machined easily can be used for the metal fastener. In this case, the first electrode can have plasma resistance and stable characteristics, while the first electrode can be manufactured at a low cost.

In the liquid treatment apparatus according to an aspect of the present disclosure, for example, the metal fastener may have a through-hole through which the gas is supplied from the gas supplier to the space.

With such a structure, the liquid treatment apparatus can easily create a state in which the first electrode is covered by a bubble. By generating plasma in this state, the liquid treatment apparatus can generate radicals efficiently and can treat a liquid in a short time.

The liquid treatment apparatus according to an aspect of the present disclosure, for example, may further include an insulator disposed in contact with an outer peripheral surface of the first electrode, the first electrode may have a tubular shape having an opening and a hollow space connected to the opening, and the gas supplier may generate the bubble in the water to be treated from the opening in the first electrode by supplying the gas to the space.

With such a structure, the liquid treatment apparatus can easily create a state in which the first electrode is covered by the gas. By generating plasma in this state, the liquid treatment apparatus can generate radicals efficiently and can treat a liquid in a short time.

A liquid treatment method according to an aspect of the present disclosure includes a step of preparing a dielectric tube, a first electrode at least a part of which is disposed in the dielectric tube, and a second electrode at least a part of which is disposed in the dielectric tube; a step of causing water to be treated to flow through the dielectric tube in such a direction that the second electrode is located upstream of the first electrode; a step of supplying a gas into the water to be treated and generating a bubble; and a step of applying a voltage between the first electrode and the at least a part of the second electrode that is located upstream of the first electrode in a state in which the bubble covers a conductor-exposed portion of the first electrode.

The liquid treatment method according to the present disclosure can improve the efficiency when treating a liquid, i.e., water to be treated, and can treat the liquid, which flows through the dielectric tube, in a short time. Note that, in the present disclosure, the term "preparing" is to be understood such that it also includes, for example, producing, purchasing, and procuring.

In the liquid treatment method according to an aspect of the present disclosure, for example, in the step of applying the voltage, the voltage may be applied in a state in which the bubble covers the conductor-exposed portion of the first electrode and the bubble is not in contact with the second electrode.

In this case, the liquid treatment method according to the present disclosure can stably cause an electrical discharge and stably generate plasma.

In the liquid treatment method according to an aspect of the present disclosure, for example, in the step of applying the voltage, an electrical discharge may be caused in the bubble and plasma may be generated.

In this case, by using the liquid treatment method, it is possible to generate plasma in the bubble, which covers the conductor-exposed portion of the first electrode in the water to be treated, and to generate radicals efficiently. Accordingly, by using the liquid treatment method, it is possible to treat a liquid in a short time.

Underlying Knowledge Forming Basis of Present Disclosure

The sterilizing apparatus described in Japanese Patent No. 4784624 vaporizes a liquid by instantaneous boiling, and generates plasma by causing an electrical discharge between a cylindrical electrode and a plate-shaped ground electrode, which are disposed so as to face each other. However, in order to cause instantaneous boiling, it is necessary to provide energy for vaporizing the liquid. Therefore, the apparatus has a problem in that it cannot efficiently generate plasma and it takes a long time to treat the liquid.

Moreover, apparatuses having existing structures treat a liquid by using electrodes that are disposed in a treatment tank for containing water to be treated. Therefore, such apparatuses have a problem in that it is difficult to reduce their size.

The inventors have devised a liquid treatment apparatus including a dielectric tube, a first electrode and a second electrode disposed in the dielectric tube, a gas supplier connected to the first electrode, and a power supply that applies a voltage between the first electrode and the second electrode. With such a structure, the liquid treatment apparatus according to the present disclosure can not only treat liquid in a short time but also realize reduction in the size of the apparatus.

Hereinafter, embodiments of the present disclosure will be described with reference to the drawings. Elements of the drawings that are the same as or equivalent to each other will be denoted by the same numerals and redundant descriptions of such elements may be omitted.

The embodiments described below are each used to describe a comprehensive or a specific example. Values, shapes, materials, elements, the arrangement of the elements, and the connection structure of the elements are only exemplary, and do not limit the scope of the present disclosure. Elements in the following embodiments that are not described in the broadest independent claim are optional.

First Embodiment

Overall Structure

A liquid treatment apparatus 100 according to a first embodiment of the present disclosure will be described.

Figure 1:
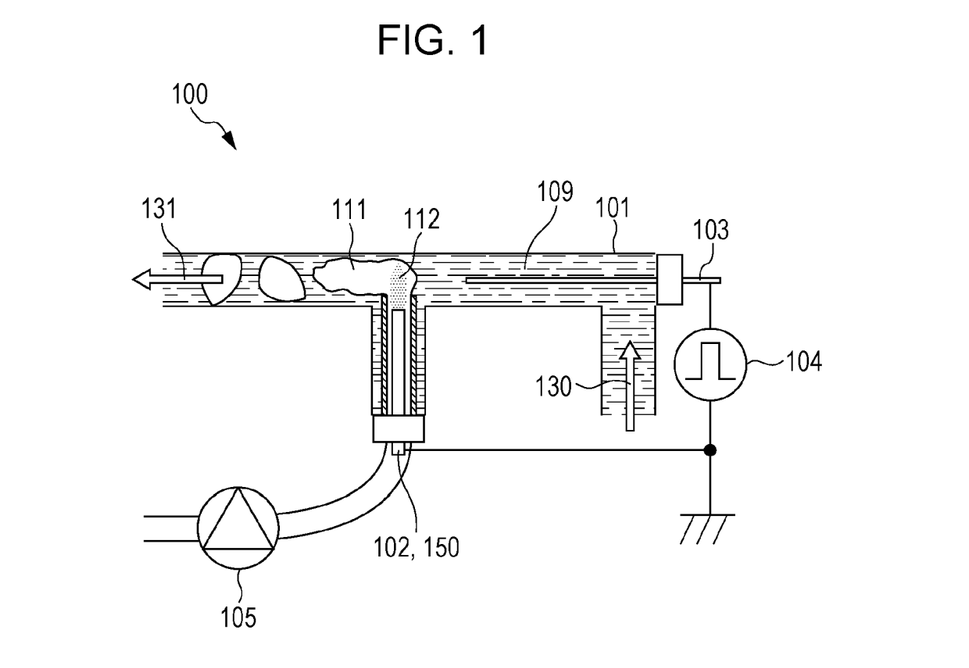
FIG. 1 is a schematic view illustrating an example of the overall structure of a liquid treatment apparatus according to a first embodiment of the present disclosure.

FIG. 1 is a schematic view illustrating an example of the overall structure of the liquid treatment apparatus 100 according to the first embodiment of the present disclosure. As illustrated in FIG. 1, the liquid treatment apparatus 100 according to the first embodiment includes a dielectric tube 101, a first electrode 102, a second electrode 103, a power supply 104, and a gas supplier 105.

As illustrated in FIG. 1, in the liquid treatment apparatus 100 according to the first embodiment, the first electrode 102 and the second electrode 103 are disposed in the dielectric tube 101. At least a part of the first electrode 102 is immersed in water 109 to be treated in the dielectric tube 101. At least a part of the second electrode 103 is immersed in the water 109 to be treated in the dielectric tube 101. The power supply 104, for applying a voltage, is connected between the first electrode 102 and the second electrode 103. The gas supplier 105, for supplying a gas 110 into the dielectric tube 101, is connected to the first electrode 102. The gas 110 forms a bubble 111 that covers the first electrode 102.

<Electrode Unit 150a Including First Electrode>

Next, an electrode unit 150 of the liquid treatment apparatus 100, including the first electrode 102, will be described. The electrode unit 150 may have a simple structure that has only the first electrode 102. The electrode unit 150 may have any appropriate structure. For example, the electrode unit 150 may include an insulator 106 that is disposed around the first electrode 102.

In the following description, an electrode unit 150a will be used as an example of the electrode unit 150 including the first electrode 102. In the electrode unit 150a, an insulator is disposed so that a space 108 is provided around a first electrode 102a.

Figure 2:
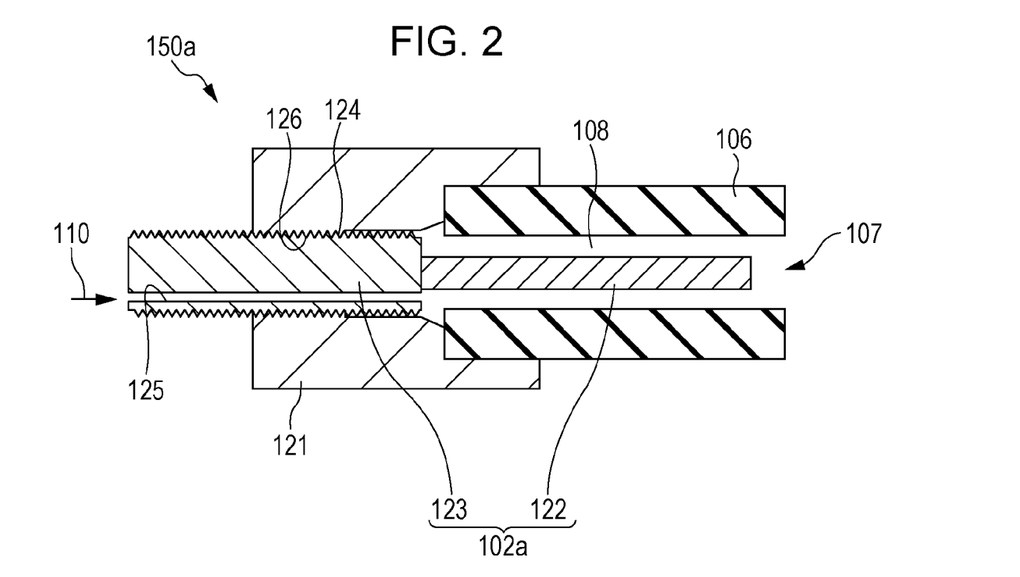
FIG. 2 is a sectional view illustrating an example of the structure of an electrode unit of the liquid treatment apparatus according to the first embodiment of the present disclosure.

FIG. 2 is a sectional view illustrating an example of the electrode unit 150a of the liquid treatment apparatus 100 according to the first embodiment of the present disclosure. As illustrated in FIG. 2, the electrode unit 150a includes the first electrode 102a, the insulator 106, and a holder block 121.

The first electrode 102a includes a metal electrode portion 122 and a metal fastener 123. The metal electrode portion 122 is disposed in the dielectric tube 101. The metal fastener 123 is connected and fixed to the holder block 121 and is connected to the power supply 104. The insulator 106 is disposed around the metal electrode portion 122 so as to form the space 108. The insulator 106 has an opening 107 through which a space inside the dielectric tube 101 is connected to the space 108 between the insulator and the metal electrode portion 122. The metal fastener 123 includes a threaded portion 124 on an outer periphery thereof and has a through-hole 125 inside thereof. The gas supplier 105 supplies the gas 110 to the space 108 through the through-hole 125, and the gas 110 is released from the opening 107 into the water 109 to be treated as the bubble 111. The holder block 121 includes a threaded portion 126, which meshes with the threaded portion 124 of the metal fastener 123, inside thereof.

Next, specific examples of the components of the liquid treatment apparatus 100 will be described.

<Dielectric Tube>

For example, the dielectric tube 101 may be made from a cylindrical silicone hose having an inside diameter of 5 mm. The dielectric tube 101 may have any appropriate shape or size as long as it is a tubular member. The cross-sectional shape of the dielectric tube 101 may be, for example, a rectangular shape, a triangular shape, or any other polygonal shape. The material of the dielectric tube 101 is not limited to silicone but may be any material that is plasma resistant and heat resistant. In the first embodiment, as illustrated in FIG. 1, the water 109 to be treated (liquid) flows from the upstream side (arrow 130) toward the downstream side (arrow 131) through the dielectric tube 101.

For example, the ratio of the length of the length of the dielectric tube 101 to the inside diameter of the dielectric tube 101 may be 5 or greater. For example, the inside diameter of the dielectric tube 101 may be 3 mm or greater. In this case, the inside diameter of the dielectric tube 101 is larger than a plasma generation field. Therefore, it is possible to suppress damage to the dielectric tube 101 due to plasma. For example, the inside diameter of the dielectric tube 101 may be 30 mm or less. In this case, the size of the liquid treatment apparatus 100 can be reduced.

<First Electrode>

At least a part of the first electrode 102a is disposed in the dielectric tube 101. As illustrated in FIG. 2, the first electrode 102a includes the metal electrode portion 122 and the metal fastener 123. The metal electrode portion 122 and the metal fastener 123 may have different sizes and may be made of different metals. For example, the metal electrode portion 122 may have a cylindrical shape having a diameter of 0.95 mm, and may be made of tungsten. For example, the metal fastener 123 may have a cylindrical shape having a diameter of 3 mm, and may be made of iron. The diameter of the metal electrode portion 122 may be any diameter with which plasma 112 can be generated. For example, the diameter may be 2 mm or less. The shape of the metal electrode portion 122 is not limited to a cylindrical shape. The metal electrode portion 122 in the dielectric tube 101 may have a columnar shape having substantially the same diameter from one end to the other end thereof. An electrode having such a shape can suppress excessive concentration of electric field at the tip thereof and can suppress deterioration with use, as compared with an electrode that is tapered toward the tip and that has substantially no thickness at the tip. The material of the metal electrode portion 122 is not limited to tungsten but may be another metal that is resistant to plasma. For example, the material of the metal electrode portion 122 may be copper, aluminum, iron, platinum, or an alloy of some of these metals. In this case, however, the durability of the metal electrode portion 122 may be reduced. Yttrium oxide to which an electroconductive substance is added may be thermally sprayed to a part of the surface of the metal electrode portion 122. Yttrium oxide to which an electroconductive substance is added has an electric resistance of, for example, 1 to 30 Ωcm. The life of an electrode can be increased by thermally spraying yttrium oxide.

The diameter of the metal fastener 123 is not limited to 3 mm but may be any appropriate diameter greater than that of the metal electrode portion 122. For example, the material of the metal fastener 123 may be any metal that can be machined easily. The material of the metal fastener 123 may be any material that is typically used for a screw, such as copper, zinc, aluminum, tin, or brass.

The first electrode 102a can be formed by, for example, pressing the metal electrode portion 122 into the metal fastener 123. As described above, a metal material that is highly resistant to plasma is used for the metal electrode portion 122 and a metal material that can be machined easily is used for the metal fastener 123. Therefore, the first electrode 102a has plasma resistance and has stable characteristics, while the first electrode 102a can be manufactured at low cost.

The through-hole 125, which is connected to the gas supplier 105, may be formed in the metal fastener 123. The through-hole 125 is also connected to the space 108, which is provided between the insulator 106 and the metal electrode portion 122. Therefore, the gas 110 from the gas supplier 105 is supplied to the space 108 through the through-hole 125. The metal electrode portion 122 is covered by the gas 110, which is supplied from the through-hole 125. The through-hole 125 may be disposed below the metal electrode portion 122 in the direction of gravity. By disposing the through-hole 125 below the metal fastener 123 in the direction of gravity, the metal electrode portion 122 can be easily covered by the gas 110 supplied from the gas supplier 105. When there are two or more through-holes 125, it is possible to suppress pressure loss at the through-holes 125. For example, the diameter of the through-hole 125 may be 0.3 mm. However, the shape and size of the through-hole 125 are not limited to these.

The threaded portion 124 may be formed on the outer periphery of the metal fastener 123. For example, if the threaded portion 124 on the outer periphery of the metal fastener 123 has a male thread, the threaded portion 126 of the holder block 121 may have a female thread. By making the threaded portion 124 mesh with the threaded portion 126, the first electrode 102a can be fixed to the holder block 121. Moreover, by rotating the metal fastener 123, the position of the end surface of the metal electrode portion 122 with respect to the opening 107 in the insulator 106 can be precisely adjusted. Furthermore, because the metal fastener 123 can be connected and fixed to the power supply 104 via the threaded portion 124, the contact resistance between the power supply 104 and the first electrode 102a can be stabilized and the characteristics of the first electrode 102a can be stabilized. If the gas supplier 105 are connected and fixed to the first electrode 102a via the threaded portion 126, the gas supplier 105 and the first electrode 102a can be reliably connected to each other. Such structures contribute to watertightness and safety when developing commercial products.

The first electrode 102a may be disposed so that the longitudinal direction of the first electrode 102a is oriented in any direction with respect to the direction in which the water 109 to be treated flows through the dielectric tube 101 (arrow 131 in FIG. 1). For example, the first electrode 102a may be disposed so that the water 109 to be treated flows through the dielectric tube 101 toward a side surface of the first electrode 102a. For example, as illustrated in FIG. 1, the first electrode 102a may be disposed so that the longitudinal direction of the first electrode 102a is perpendicular to the direction in which the water 109 to be treated flows through the dielectric tube 101 (arrow 131 in FIG. 1). When the first electrode 102a is disposed as illustrated in FIG. 1, it is possible to suppress the stationary state of the bubble 111 around the first electrode 102a. The bubble 111 is formed, for example, by the gas 110 supplied from the gas supplier 105.

In other words, as illustrated in FIG. 1, the longitudinal direction of the first electrode 102a may cross, in the dielectric tube 101, the direction in which the water 109 to be treated flows from the second electrode 103 toward the first electrode 102a. In this case, it is possible to suppress the stationary state of the bubble 111 around the first electrode 102a. Note that it is sufficient that the longitudinal direction of the first electrode 102a and the direction of the flow of the water 109 to be treated cross each other as vectors. For example, one end of the first electrode 102a may or may not actually protrude into a flow path.

<Second Electrode>

At least a part of the second electrode 103 is disposed in the dielectric tube 101. For example, the second electrode 103 may have a cylindrical shape having a diameter of 1 mm and may be made of tungsten. The shape, size, and material of the second electrode 103 are not limited to these. The second electrode 103 may be made of any electroconductive metal material. For example, as with the first electrode 102a, the material of the second electrode 103 may be iron, tungsten, copper, aluminum, platinum, or an alloy including one or more of these metals.

For example, the distance between the first electrode 102a and the second electrode 103 may be 10 mm. The distance between the first electrode 102a and the second electrode 103 is not limited to this and may be any distance with which the plasma 112 can be generated. The liquid treatment apparatus 100, which includes the dielectric tube 101, has the following characteristic: as the flow path of the water 109 to be treated becomes limited, the electric resistance between the first electrode 102a and the second electrode 103 increases and it becomes more difficult to cause an electrical discharge between the first electrode 102a and the second electrode 103. Therefore, the distance between the electrodes may be appropriately set in accordance with the inside diameter of the dielectric tube 101, which defines the flow path. For example, the distance between the first electrode 102a and the second electrode 103 may be, for example, 1 mm or greater and 15 mm or less. When the inside diameter of the dielectric tube 101 is 5 mm, the distance between the first electrode 102a and the second electrode 103 may be in the range of 5 to 15 mm.

The second electrode 103 is disposed in the dielectric tube 101 at a position upstream of the first electrode 102a. With such an arrangement, the liquid treatment apparatus 100 according to the first embodiment can efficiently generate the plasma 112.

<Insulator>

The insulator 106 is disposed so that the space 108 is provided around the metal electrode portion 122 of the first electrode 102a. The gas 110 is supplied to the space 108 from the gas supplier 105, and the metal electrode portion 122 is covered by the gas 110. Accordingly, the outer peripheral surface of the metal electrode portion 122 does not directly contact the water 109 to be treated, although a conductor-exposed portion, which is a metal portion of the electrode, is exposed. The insulator 106 may have, for example, a cylindrical shape having an inside diameter of 1 mm. However, the size and shape of the insulator 106 are not limited to these.

The insulator 106 has the opening 107. The opening 107 has a function of determining the size of the bubble 111 when the bubble 111 is released into the water 109 to be treated in the dielectric tube 101. For example, the material of the insulator 106 may be an alumina ceramic (i.e., aluminum oxide), magnesium oxide, yttrium oxide, an insulating plastic, glass, quartz, or the like.

As illustrated in FIG. 2, the opening 107 in the insulator 106 may be provided in an end surface of the insulator 106. Alternatively, the opening 107 may be provided in a side surface of the insulator 106. The position of the opening 107 is not particularly limited. The insulator 106 may have a plurality of openings 107. For example, the opening 107 in the insulator 106 may have a circular shape having a diameter of 1 mm. However, the shape and size of the opening 107 are not limited to these. For example, the diameter of the opening 107 may be in the range of 0.3 mm to 2 mm.

<Power Supply>

The power supply 104 can apply a voltage between the first electrode 102a and the second electrode 103. The power supply 104 can apply a pulse voltage or an alternating-current voltage between the first electrode 102a and the second electrode 103. The waveform of the voltage may be, for example, a pulse, a half-sine waveform, or a sine waveform. The power supply 104 may apply a so-called bipolar pulse voltage, in which a positive pulse voltage and a negative pulse voltage are alternately applied. For example, the power supply 104 may have an output capacity of 80 VA and may apply a peak voltage of 10 kV when unloaded.

<Gas Supplier>

The gas supplier 105 is connected to the metal fastener 123 of the first electrode 102a. The gas supplier 105 supplies the gas 110 to the space 108 through the through-hole 125 in the metal fastener 123. The gas 110 is, for example, air, He, Ar, $O_2$, or the like. In first embodiment, the amount of gas supplied from the gas supplier 105 is not particularly limited. The gas supplier 105 may be capable of, for example, supplying a gas in the amount of 1 liter/min. As the gas supplier 105, for example, a pump or the like may be used. In the example illustrated in FIG. 2, the bubble 111 is formed by the gas 110 supplied from the gas supplier 105. The bubble 111 covers the surface of the metal electrode portion 122, which is a conductor-exposed portion of the first electrode 102a.

The gas supplier 105 may, for example, supply the gas to the flow path, along which the water 109 to be treated flows through the dielectric tube 101, from below in the direction of gravity.

<Holder Block>

The holder block 121 is connected to the metal fastener 123 of the first electrode 102a and is connected to the insulator 106. The holder block 121 may have a sealing structure for preventing the water 109 to be treated from leaking from a position at which the holder block 121 is connected to the first electrode 102a and/or a position at which the holder block 121 is connected to the insulator 106. For example, the holder block 121 may have a structure including the threaded portion 126 therein, into which the metal fastener 123 of the first electrode 102a is screwed and fixed. The holder block 121 may have a structure including a threaded portion (not shown) therein, into which the insulator 106 is screwed and fixed. The sealing structure is not limited to this and may be any appropriate structure.

In the present disclosure, the phrase "a surface of the metal electrode portion does not directly contact the water to be treated" means that the surface of the metal electrode portion does not contact the mass of liquid in the dielectric tube. Accordingly, a state in which "the metal electrode portion does not directly contact the water to be treated" includes a state in which the surface of the metal electrode portion is wet with the water to be treated (in a strict sense, the surface of the metal electrode portion is in contact with the water to be treated and the gas in the bubble covers the surface. Such a state occurs, for example, when a bubble is generated in a state in which the surface of the first electrode is wet with a liquid.

[Operation (Liquid Treatment Method)]

An operation of the liquid treatment apparatus 100 according to the first embodiment, that is, an example of a liquid treatment method performed by the liquid treatment apparatus 100 according to the first embodiment will be described.

The water 109 to be treated is supplied into the dielectric tube 101. The water 109 to be treated supplied into the dielectric tube 101 flows through the dielectric tube 101 from the upstream side (arrow 130 in FIG. 1) toward the downstream side (arrow 131 in FIG. 1).

The gas supplier 105 supplies the gas 110 through the through-hole 125 of the first electrode 102a to the space 108 provided between the insulator 106 and the metal electrode portion 122 of the first electrode 102a. The gas 110 is released from the opening 107 in the insulator 106 into the water 109 to be treated in the dielectric tube 101. As a result, the bubble 111 that covers the metal electrode portion 122 of the first electrode 102a (e.g., conductor-exposed portion) is formed in the water 109 to be treated as described above. In other words, the bubble 111 is generated from the opening 107 in the insulator 106. Thus, the metal electrode portion 122 of the first electrode 102a can be always in a state in which it is covered by the bubble 111 formed from the gas 110.

In the state in which the metal electrode portion 122 is covered by the bubble 111, the power supply 104 applies a voltage between the first electrode 102a and the second electrode 103. When the voltage is applied between the first electrode 102a and the second electrode 103, an electrical discharge occurs in the bubble 111. Due to the electrical discharge, the plasma 112 is generated in the bubble 111 from a region near the metal electrode portion 122 of the first electrode 102a. Due to the plasma 112, OH radicals and the like are generated in the water 109 to be treated, and the radicals and the like sterilize the water 109 to be treated and/or decompose chemical substances in the water 109 to be treated. The plasma 112 is generated not only at an end portion of the first electrode 102a in the bubble 111 but also in a wide area in the space 108. This is because the water 109 to be treated functions as a counter electrode via the insulator 106. Due to such an effect, a large amount of ions are generated, thereby generating a large amount of radicals in the water 109 to be treated. This is a great advantage obtained by using the structure according the present disclosure, in which the first electrode 102a is located in the water 109 to be treated. The liquid treatment apparatus 100 can generate OH radicals having a long life.

Note that the "life" of OH radicals is measured in the following way. First, the amount of OH radicals in a liquid is measured by using the ESR (electron spin resonance) method at regular intervals after generation of the plasma 112 has been stopped. Next, the half-life of OH radicals is calculated from a change of the measured amount of OH radicals with time. The half-life of OH radicals obtained in this way is referred to as the "life" of OH radicals in the present disclosure. The inventors found that OH radicals having a life of about 5 minutes can be obtained by using the liquid treatment apparatus 100 according to the first embodiment.

[Relationship Between Arrangement of First Electrode and Second Electrode and Effect]

The relationship between the arrangement of the first electrode and the second electrode and its effect in the liquid treatment apparatus 100 according to the first embodiment will be described. In the first embodiment, the second electrode 103 is disposed upstream of the first electrode 102a in the dielectric tube 101. The distance between the first electrode 102a and the second electrode 103 may be, for example, 10 mm. With such an arrangement, the liquid treatment apparatus 100 according to the first embodiment can efficiently generate the plasma 112.

Figure 3:
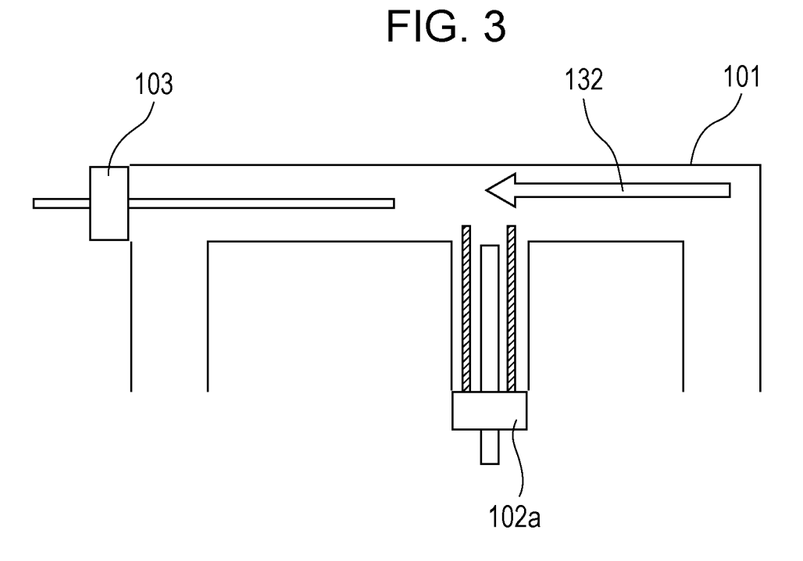
FIG. 3 is a schematic view illustrating a comparative example 1 of the arrangement of a first electrode and a second electrode.
Figure 4:
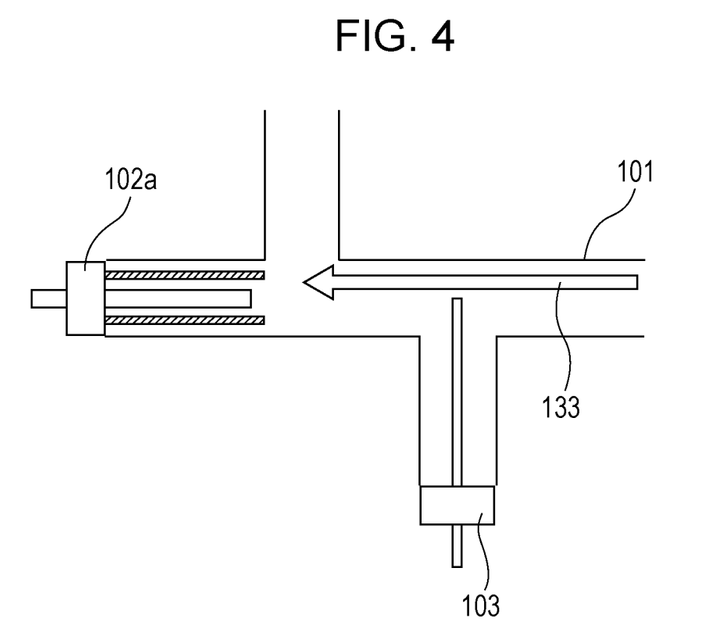
FIG. 4 is a schematic view illustrating a comparative example 2 of the arrangement of the first electrode and the second electrode.
Figure 5:
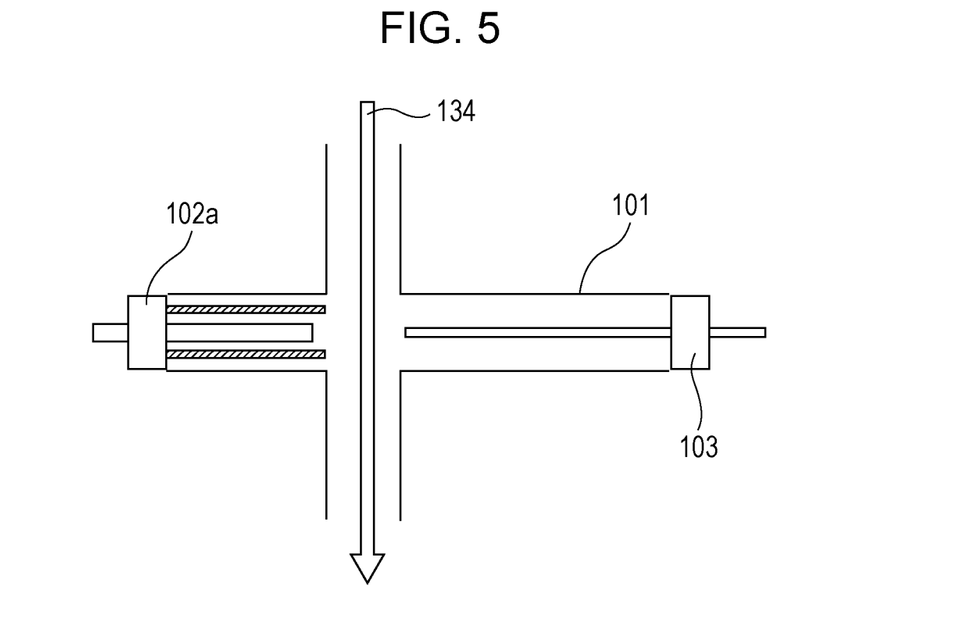
FIG. 5 is a schematic view illustrating a comparative example 3 of the arrangement of the first electrode and the second electrode.

Cases where the arrangement of the first electrode 102a and the second electrode 103 differs from that shown in FIG. 1 will be described by using comparative examples 1 to 3. FIG. 3 illustrates the arrangement of the first electrode 102a and the second electrode 103 in the comparative example 1. FIG. 4 illustrates the arrangement of the first electrode 102a and the second electrode 103 in the comparative example 2. FIG. 5 illustrates the arrangement of the first electrode 102a and the second electrode 103 in the comparative example 3.

Except for the arrangement of the first electrode 102a and the second electrode 103, the following structures and conditions were used in the comparative examples 1 to 3.

Conditions Common to Comparative Examples 1 to 3

The comparative examples 1 to 3 each had a structure similar to the overall structure shown in FIG. 1, except for the shapes of the electrode unit 150a, the second electrode 103, and the dielectric tube 101. The comparative examples 1 to 3 each included the electrode unit 150a shown in FIG. 2. The dielectric tube 101 was made from a cylindrical silicon hose having an inside diameter of 5 mm. The metal electrode portion 122 of the first electrode 102 had a cylindrical shape having a diameter of 0.95 mm and was made of tungsten. The metal fastener 123 of the first electrode 102 had a cylindrical shape having a diameter of 3 mm and was made of iron. The diameter of the through-hole 125 provided in the metal fastener 123 of the first electrode 102 was 0.3 mm. The insulator 106 had a cylindrical shape having an inside diameter of 1 mm and was made of an alumina ceramic (i.e., aluminum oxide). The diameter of the opening 107 in the insulator 106 was 1 mm. The second electrode 103 had a cylindrical shape having a diameter of 1 mm and was made of tungsten. The distance between the first electrode 102a and the second electrode 103 was 10 mm. The power supply 104 had an output capacity of 80 VA and was capable of applying a peak voltage of 10 kV when unloaded. The amount of gas supplied from the gas supplier 105 was 0.2 liter/min.

Comparative Example 1

The comparative example 1, which is illustrated in FIG. 3, will be described. As illustrated in FIG. 3, the second electrode 103 of the comparative example 1 was disposed downstream of the first electrode 102a in the dielectric tube 101. The first electrode 102a of the comparative example 1 was disposed so that the longitudinal direction of the first electrode 102a crossed a direction 132 in which the water 109 to be treated flowed through the dielectric tube 101. The second electrode 103 of the comparative example 1 was disposed so that the longitudinal direction of the second electrode 103 was the same as the direction 132 in which the water 109 to be treated flowed through the dielectric tube 101.

In the comparative example 1 having the above structure, the bubble 111 generated from the first electrode 102a flowed in a direction 132 in which the water 109 to be treated flowed. In other words, the bubble 111 generated from the first electrode 102a flowed toward the second electrode 103. Accordingly, in the comparative example 1, the bubble 111 was present in the path of electric current between the first electrode 102a and the second electrode 103. Therefore, it occasionally happened that the bubble 111 covered the first electrode 102a and the second electrode 103 simultaneously. When the power supply 104 applied a voltage between the first electrode 102a and the second electrode 103 in this state, an arc discharge occurred between the electrodes in the bubble 111. Accordingly, with the arrangement of the first electrode 102a and the second electrode 103 of the comparative example 1, the plasma 112 could not be stably generated.

As described above, in the first embodiment and the comparative examples 1 to 3, the distance between the first electrode 102a and the second electrode 103 is set to be small (for example, 15 mm or less) so that an electrical discharge can occur in the dielectric tube 101. A compared with a treatment tank, which has a large volume, the flow path in the dielectric tube 101 may be easily filled with the bubble 111 generated therein. Thus, as the distance between the first electrode 102a and the second electrode 103 becomes smaller and/or as the ratio of the volume of the flow path occupied by the bubble 111 becomes higher, it becomes more likely that the bubble 111, which covers the first electrode 102a, also covers the second electrode 103 simultaneously. In other words, although the size of the liquid treatment apparatus 100, which includes the dielectric tube 101, can be reduced, the probability that the bubble 111 covers the first electrode 102a and the second electrode simultaneously is increased. Therefore, plasma might not be stably generated.

Comparative Example 2

The comparative example 2, which is illustrated in FIG. 4, will be described. As illustrated in FIG. 4, the second electrode 103 of the comparative example 2 was disposed upstream of the first electrode 102a. The first electrode 102a of the comparative example 2 was disposed so that the longitudinal direction of the first electrode 102a was the same as a direction 133 in which the water 109 to be treated flowed through the dielectric tube 101. In other words, the first electrode 102a of the comparative example 2 was disposed so that the longitudinal direction of the first electrode 102a was the same as the direction 133 in which the water 109 to be treated flowed from the second electrode 103 toward the first electrode 102a. The first electrode 102a of the comparative example 2 was disposed downstream of the dielectric tube 101. The second electrode 103 of the comparative example 2 was disposed so that the longitudinal direction of the second electrode 103 was perpendicular to the direction 133 in which the water 109 to be treated flowed through the dielectric tube 101.

In the comparative example 2 having the above structure, the bubble 111 generated from the first electrode 102a was pushed back by the water 109 to be treated, which flowed through the dielectric tube 101, in the direction 133 in which the water 109 to be treated flowed. Therefore, the bubble 111 generated from the first electrode 102a became stationary around the first electrode 102a. As a result, in the comparative example 2, when the power supply 104 applied a voltage between the first electrode 102a and the second electrode 103, an electrical discharge did not occur stably. Accordingly, in the comparative example 2, the plasma 112 could not be stably generated. In the comparative example 2, in which the bubble 111 became stationary around the first electrode 102a, where the plasma 112 was generated, heat generated during generation of the plasma 112 was not smoothly dissipated.

Comparative Example 3

The comparative example 3, which is illustrated in FIG. 5, will be described. As illustrated in FIG. 5, the first electrode 102a of the comparative example 3 was disposed so as to face the second electrode 103. The first electrode 102a of the comparative example 3 was disposed so that the longitudinal direction of the first electrode 102a was perpendicular to a direction 134 in which the water 109 to be treated flowed through the dielectric tube 101. The second electrode 103 of the comparative example 3 was disposed so that the longitudinal direction of the second electrode 103 was perpendicular to the direction 134 in which the water 109 to be treated flowed through the dielectric tube 101. The second electrode 103 of the comparative example 3 was disposed so as to face the first electrode 102a.

In the comparative example 3 having the above structure, it happened that the bubble 111 generated from the first electrode 102a covered the first electrode 102a and the second electrode 103 simultaneously. Therefore, in the comparative example 3, when the power supply 104 applied a voltage between the first electrode 102 and the second electrode 103, an arc discharge occurred. Accordingly, in the comparative example 3, the plasma 112 could not be stably generated.

As described above, with the arrangements of the first electrode 102a and the second electrode 103 in the comparative examples 1 to 3, an electrical discharge did not stably occur in the bubble 111 in the water 109 to be treated and the plasma 112 could not be stably generated. Moreover, the comparative example 2, in which heat generated when the plasma 112 was generated was not efficiently dissipated, was disadvantageous for cooling.

Example

An example of the liquid treatment apparatus 100 illustrated in FIG. 1 was examined. The example had a structure the same as the overall structure shown in FIG. 1 and included the electrode unit 150a shown in FIG. 2. Except for the shapes of the electrode unit 150a, the second electrode 103, and the dielectric tube 101, the conditions were the same as those of comparative examples 1 to 3.

In the example of the liquid treatment apparatus 100 illustrated in FIG. 1, the second electrode 103 was disposed upstream of the first electrode 102a. The first electrode 102a was disposed so that the longitudinal direction of the first electrode 102a was perpendicular to the direction 131 in which the water 109 to be treated flowed through the dielectric tube 101. Therefore, in the liquid treatment apparatus 100 illustrated in FIG. 1, the bubble 111 generated from the first electrode 102 did not contact the second electrode 103. Therefore, the liquid treatment apparatus 100 could stably cause an electrical discharge (e.g., glow discharge) when a voltage was applied between the first electrode 102a and the second electrode 103. As a result, with the arrangement of the first electrode 102a and the second electrode 103 in the liquid treatment apparatus 100, the plasma 112 could be stably generated. With the arrangement of the first electrode 102a and the second electrode 103 in the liquid treatment apparatus 100, the bubble 111 generated from the first electrode 102a flowed downstream through the dielectric tube 101 without becoming stationary around the first electrode 102a. Therefore, heat generated when the plasma 112 was generated could be efficiently dissipated and cooled.

In the liquid treatment apparatus 100 illustrated in FIG. 1, the first electrode 102a is disposed so that the longitudinal direction of the first electrode 102a was perpendicular to the direction 131 in which the water 109 to be treated flows through the dielectric tube 101. However, in a liquid treatment apparatus according to the first embodiment, the orientation of the first electrode is not limited to this. For example, the first electrode 102a may be disposed so that the longitudinal direction of the first electrode 102a forms an angle of, for example, 45° with the direction 131 in which the water 109 to be treated flows. As long as the bubble 111 does not become stationary around the first electrode 102a, the first electrode 102a may be disposed so as to form any appropriate angle with the direction 131 in which the water 109 to be treated flows.

In the liquid treatment apparatus 100 illustrated in FIG. 1, the second electrode 103 is disposed so that the longitudinal direction of the second electrode 103 is the same as the direction 131 in which the water 109 to be treated flows through the dielectric tube 101. However, in a liquid treatment apparatus according to the first embodiment, the orientation of the second electrode is not limited to this. As long as the second electrode 103 is disposed upstream of the first electrode 102a, the orientation of the second electrode 103 is not particularly limited.

In the first embodiment, the distance between the first electrode 102a and the second electrode 103 may be any appropriate distance with which the plasma 112 can be generated.

[Effect of Treatment of Liquid Using Dielectric Tube]

The rate of treating a liquid by using the liquid treatment apparatus 100 according to the first embodiment will be described. Here, the results of experiments of measuring the decomposition rate in a case where a liquid was treated by using the example of the liquid treatment apparatus 100 including the dielectric tube 101 and in a case where the liquid was treated by using a reference example of a liquid treatment, which included a treatment tank instead of the dielectric tube 101, will be described. The experiment was performed by treating an indigo carmine aqueous solution by using each of the apparatuses and measuring the time required for decomposing the indigo carmine aqueous solution.

Example

The example of the liquid treatment apparatus had a structure the same as the overall structure illustrated in FIG. 1 and included the electrode unit 150a illustrated in FIG. 2. The dielectric tube 101 was made from a cylindrical silicon hose having an inside diameter of 5 mm. The metal electrode portion 122 of the first electrode 102 had a cylindrical shape having a diameter of 0.95 mm and was made of tungsten. The metal fastener 123 of the first electrode 102 had a cylindrical shape having a diameter of 3 mm and was made of iron. The diameter of the through-hole 125 provided in the metal fastener 123 of the first electrode 102 was 0.3 mm. The insulator 106 had a cylindrical shape having an inside diameter of 1 mm and was made of an alumina ceramic (i.e., aluminum oxide). The diameter of the opening 107 in the insulator 106 was 1 mm. The second electrode 103 had a cylindrical shape having a diameter of 1 mm and was made of tungsten. The distance between the first electrode 102a and the second electrode 103 was 10 mm. The power supply 104 had an output capacity of 80 VA and was capable of applying a peak voltage of 10 kV when unloaded. The amount of gas supplied from the gas supplier 105 was 0.2 liter/min.

Reference Example

The reference example will be described. The reference example differs from the example in that the reference example includes a treatment tank that has a larger volume than the dielectric tube 101. The reference example had a structure in which the first electrode 102a and the second electrode 103 were disposed in the treatment tank, which was filled with the water 109 to be treated. The treatment tank of the reference example had a volume of 0.2 liter. Structures of the other parts and the conditions for the reference example were the same as those of the example.

Figure 6:
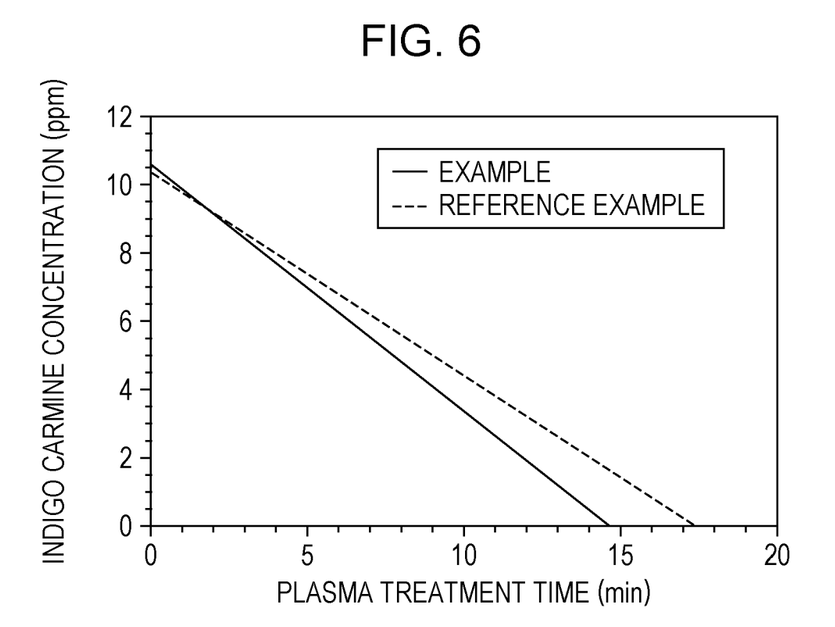
FIG. 6 is a graph representing a change over time of the indigo carmine concentration in the liquid treatment apparatus according to an example of the first embodiment of the present disclosure and in a liquid treatment apparatus according to a reference example.

FIG. 6 is a graph representing a change over time of the indigo carmine concentration in the cases where an indigo carmine aqueous solution was treated by using the liquid treatment apparatus according to the example and the liquid treatment apparatus according to the reference example. In FIG. 6, the vertical axis represents indigo carmine concentration (ppm), and the horizontal axis represents time (min). In FIG. 6, the dotted line represents the reference example, and the solid line represents the example.

As illustrated in FIG. 6, it was found that the composition rate in the example was higher that that of the reference example. This is because, in the example, OH radicals generated by the plasma 112 can more easily contact indigo carmine in the aqueous solution than in the reference example. The details will be described below.

First, the reference example will be described. In the reference example, the water 109 to be treated, which was contained in the treatment tank, was treated. In the reference example, the bubble 111 was generated in the indigo carmine aqueous solution contained in the treatment tank, and OH radicals were generated by generating the plasma 112 in the bubble 111. However, in the reference example, contact between OH radicals and indigo carmine in the treatment tank easily occurred in a region near the first electrode 102a, where the plasma 112 was generated, but did not easily occur in other regions. Accordingly, in the reference example, there were a region in the treatment tank where a reaction between OH radicals and indigo carmine easily occurred and a region in which such reaction did not easily occur. Therefore, it occasionally occurred that the water 109 to be treated could not be efficiently treated.

Next, the example will be described. In the example, liquid treatment was performed while an indigo carmine aqueous solution flowed through the dielectric tube 101 having an inside diameter of 5 mm. In the example, there were a large number of bubbles 111 in a part of the flow path in the dielectric tube 101 downstream of the first electrode 102a. Accordingly, in the example, a part of the indigo carmine aqueous solution flowing downstream from the first electrode 102a could easily contact the bubble 111. Therefore, it is considered that contact between OH radicals and indigo carmine occurred in a region near the interface between the indigo carmine aqueous solution and the bubble 111. As a result, it is considered that, in the example, a reaction between OH radicals and indigo carmine easily occurred, and therefore the decomposition rate was higher than that of the reference example.

As described above, the liquid treatment apparatus 100 according to the first embodiment can efficiently generate OH radicals by using the plasma 112. The liquid treatment apparatus 100 according to the first embodiment can treat the water 109 to be treated in a short time by, for example, efficiently causing reactions between OH radicals and bacteria, chemical substances, or the like in the water 109 to be treated.

Second Embodiment

A liquid treatment apparatus according to a second embodiment will be described.

Only the difference between the second embodiment and the first embodiment will be described, and descriptions of the same elements will be omitted.

Figure 7:
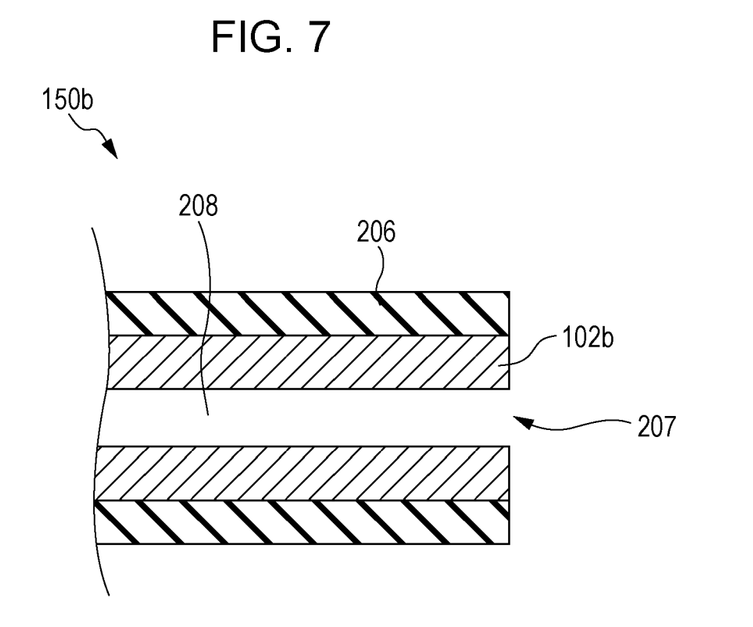
FIG. 7 is a sectional view illustrating an example of the structure of an electrode unit of a liquid treatment apparatus according to a second embodiment of the present disclosure.

FIG. 7 is a sectional view illustrating an example of the structure of an electrode unit 150b of the liquid treatment apparatus according to the second embodiment of the present disclosure. As illustrated in FIG. 7, the electrode unit 150b according to the second embodiment includes an insulator 206, which is disposed so as to cover a first electrode 102b. The second embodiment differs from the first embodiment in the shape of the first electrode 102b and the arrangement of the insulator 206. Except for these, the second embodiment has the same structure as the first embodiment. The electrode unit 150b according to the second embodiment will be described below.

[Electrode Unit 150b Including First Electrode]

As illustrated in FIG. 7, the electrode unit 150b according to the second embodiment includes the first electrode 102b and the insulator 206. The first electrode 102b is made from a hollow tubular metal material. The first electrode 102b may have, for example, an inside diameter of 0.4 mm and an outside diameter of 0.6 mm. The first electrode 102b has an opening 207 at an end thereof and a space 208 inside thereof. The insulator 206 is disposed in contact with an outer peripheral surface of the first electrode 102b, and there is no gap between the insulator 206 and the first electrode 102b. Metal portions are exposed only at an end surface and at an inner peripheral surface of the first electrode 102b. Because the insulator 206 is disposed on the outer peripheral surface of the first electrode 102b with no gap therebetween, the outer peripheral surface of the first electrode 102b does not directly contact the water 109 to be treated. For example, the insulator 206 may have a thickness of 0.1 mm.

[Operation (Liquid Treatment Method)]

An operation of the liquid treatment apparatus according to the second embodiment, that is, a liquid treatment method performed by using the liquid treatment apparatus according to the second embodiment will be described.

The water 109 to be treated is supplied into the dielectric tube 101. The water 109 to be treated supplied into the dielectric tube 101 flows through the dielectric tube 101 from the upstream side (arrow 130 in FIG. 1) toward the downstream side (arrow 131 in FIG. 1).

The gas supplier 105 supplies the gas 110 to the space 208 in the first electrode 102b. The gas 110 is released from the opening 207 in the first electrode 102b into the water 109 to be treated in the dielectric tube 101. As a result, the bubble 111 is formed in the water 109 to be treated in the dielectric tube 101. The bubble 111 covers the opening 207 in the first electrode 102b with the gas 110 inside thereof. The bubble 111 is formed over a certain distance from the opening 207 in the first electrode 102b. Thus, in the second embodiment, the opening 207 in the first electrode 102b also functions as a bubble generator. By adjusting the amount of the gas 110 supplied from the gas supplier 105, it is possible to create a state in which a region around the opening 207 in the first electrode 102b, that is, an end surface of the first electrode 102b from which metal is exposed is covered with the gas in the bubble 111. In the bubble 111, which covers the end surface of the first electrode 102b, a gas-liquid interface, along which the gas 110 in the bubble 111 contacts the water 109 to be treated around the bubble 111, is defined not only in the liquid but also by an interface along which the gas 110 in the bubble 111 and the insulator 206 contact each other. In other words, the gas-liquid interface defining the bubble 111 is not "closed" in the water 109 to be treated. The bubble 111 is in contact with the insulator 206 near the opening 207 in the first electrode 102b. As described above, in the outer surface of the first electrode 102b, the conductor is exposed only at an end surface near the opening 207. Therefore, by generating the bubble 111 that covers the end surface, the outer surface of the first electrode 102b is separated from the water 109 to be treated by the bubble 111 and the insulator 206. The inner peripheral surface of the first electrode 102b does not directly contact the water 109 to be treated, because the inner peripheral surface is covered by the gas 110 supplied when the bubble 111 is formed.

Next, in the state in which the conductor-exposed portion of the first electrode 102b is covered by the bubble 111, the power supply 104 applies a voltage between the first electrode 102b and the second electrode 103. When the voltage is applied between the first electrode 102b and the second electrode 103, an electric discharge occurs in the bubble 111 and plasma is generated near the first electrode 102b. The plasma spreads in the entirety of the bubble 111. In particular, high-concentration plasma 112 is generated near the first electrode 102b. Plasma is generated also in the hollow space 208 in the first electrode 102b. Therefore, not only the end of the electrode but also the entirety of the electrode can be efficiently used.

[Advantages]

The liquid treatment apparatus according to the second embodiment includes the electrode unit 150b, which includes the first electrode 102b, and the gas supplier 105, which supplies the gas 110 to the space 208 in the first electrode 102b. Thus, the liquid treatment apparatus according to the second embodiment can generate the bubble 111 from the opening 207 in the first electrode 102b. Moreover, the liquid treatment apparatus according to the second embodiment can generate OH radicals having a long life by causing an electrical discharge in the bubble 111 and generating the plasma 112. Accordingly, also with the second embodiment, it is possible to efficiently generate the plasma 112 in the bubble 111 and to treat the water 109 to be treated in a short time.

In a liquid treatment apparatus according to the present disclosure, a first electrode and a second electrode are disposed in an electric tube through which water to be treated flows. The second electrode is disposed upstream of the first electrode. A gas supplier that supplies a gas is connected to the first electrode. The liquid treatment apparatus includes a power supply that applies a voltage between the first electrode and the second electrode. With such a structure, the liquid treatment apparatus according to the present disclosure can supply the gas from the gas supplier to a position near the first electrode and can generate a bubble that covers a conductor-exposed portion of the first electrode. Therefore, the liquid treatment apparatus according to the present disclosure can efficiently generate plasma in the bubble generated in the water to be treated when the voltage is applied between the first electrode and the second electrode.

Accordingly, the liquid treatment apparatus according to the present disclosure can, by using OH radicals generated by the plasma, efficiently kill bacteria in the water to be treated and/or efficiently decompose chemical substances and the like in the water to be treated. Therefore, the liquid treatment apparatus according to the present disclosure can treat water to be treated (liquid) in a short time.

The liquid treatment apparatus according to the present disclosure can treat water to be treated while the water to be treated flows through the dielectric tube. Therefore, the apparatus can be made smaller than existing liquid treatment apparatuses, which include a treatment tank.

The structure of the liquid treatment apparatus according to the present disclosure is not limited to those described above, and various other structures may be used. The electrode unit, including the first electrode, may have any structure that can generate radicals by generating plasma in a liquid.

The first electrode described above is disposed so as to be perpendicular to the direction in which a liquid flows through the dielectric tube. However, a first electrode of the liquid treatment apparatus according to the present disclosure may be disposed so as to form any appropriate angle with the dielectric tube. For example, the first electrode may be disposed in such a way that the longitudinal direction of the first electrode is not parallel to the direction in which the liquid flows through the dielectric tube.

The liquid treatment apparatus and the liquid treatment method according to the present disclosure can be used as a liquid treatment apparatus for, for example, an air conditioner, a humidifier, an electric shaver cleaner, a dishwasher, a water treatment apparatus for hydroponics, a nutrient solution circulator, a water-cleaning toilet, a water purifier, a washing machine, an electric kettle, or an air purifier.

While the present disclosure has been described with respect to exemplary embodiments thereof, it will be apparent to those skilled in the art that the disclosure may be modified in numerous ways and may assume many embodiments other than those specifically described above. Accordingly, it is intended by the appended claims to cover all modifications of the disclosure that fall within the true spirit and scope of the disclosure.

What is claimed is:

1. A liquid treatment apparatus comprising:
   a dielectric tube through which water to be treated flows;
   a first electrode at least a part of which is disposed in the dielectric tube;
   a second electrode at least a part of which is disposed in the dielectric tube at a position upstream of the first electrode;
   a gas supplier operative to generate a bubble by supplying a gas into the water to be treated; and
   a power supply operative to apply a voltage between the first electrode and the second electrode in a state in which the bubble covers a conductor-exposed portion of the first electrode, wherein
   each of the first and second electrodes has a rod shape, a longitudinal axis of the first electrode is perpendicular to a longitudinal direction of the dielectric tube, and
the second electrode is parallel to the longitudinal direction of the dielectric tube.

2. The liquid treatment apparatus according to claim 1, wherein
a flow path of the water to be treated extends parallel to the longitudinal direction of the dielectric tube, and
the longitudinal axis of the first electrode crosses the flow path of the water to be treated.

3. The liquid treatment apparatus according to claim 1, wherein the power supply is operative to apply the voltage in a state in which the bubble is not in contact with the second electrode.

4. The liquid treatment apparatus according to claim 1, wherein the power supply is operative to apply a voltage between the first electrode and the second electrode to cause an electrical discharge in the bubble and generate plasma.

5. The liquid treatment apparatus according to claim 1, wherein the dielectric tube defines a flow path through which the water to be treated flows from the second electrode toward the first electrode and through which the water to be treated and the bubble flow downstream from the first electrode.

6. The liquid treatment apparatus according to claim 1, further comprising:
an insulator that surrounds the first electrode with a space therebetween in the dielectric tube, the insulator including an opening through which the space is connected to an inside of the dielectric tube,
wherein the gas supplier is operative to generate the bubble in the water to be treated from the opening in the insulator by supplying the gas to the space.

7. The liquid treatment apparatus according to claim 6, wherein the first electrode includes a metal electrode portion disposed in the dielectric tube and a metal fastener that fixes the first electrode in place and that is connected to the power supply, and
wherein the metal electrode portion and the metal fastener contain different materials.

8. The liquid treatment apparatus according to claim 7, wherein the metal fastener has a through-hole through which the gas is supplied from the gas supplier to the space.

9. The liquid treatment apparatus according to claim 1, further comprising:
an insulator disposed in contact with an outer peripheral surface of the first electrode,
wherein the first electrode has a tubular shape including an opening and a hollow space connected to the opening, and
wherein the gas supplier is operative to generate the bubble in the water to be treated from the opening in the first electrode by supplying the gas to the space.

10. A liquid treatment method comprising:
(a) preparing a dielectric tube, a first electrode at least a part of which is disposed in the dielectric tube, and a second electrode at least a part of which is disposed in the dielectric tube;
(b) causing water to be treated to flow through the dielectric tube in a direction that the second electrode is located upstream of the first electrode;
(c) supplying a gas into the water to be treated and generating a bubble; and
(d) applying a voltage between the first electrode and the second electrode in a state in which the bubble covers a conductor-exposed portion of the first electrode, wherein
each of the first and second electrodes has a rod shape,
a longitudinal axis of the first electrode is perpendicular to a longitudinal direction of the dielectric tube, and
the second electrode is parallel to the longitudinal direction of the dielectric tube.

11. A liquid treatment method comprising:
(a) preparing a dielectric tube, a first electrode at least a part of which is disposed in the dielectric tube, and a second electrode at least a part of which is disposed in the dielectric tube;
(b) causing water to be treated to flow through the dielectric tube in a direction that the second electrode is located upstream of the first electrode;
(c) supplying a gas into the water to be treated and generating a bubble; and
(d) applying a voltage between the first electrode and the second electrode in a state in which the bubble covers a conductor-exposed portion of the first electrode,
wherein, in the step (d), the voltage is applied in a state in which the bubble is not in contact with the second electrode.

12. The liquid treatment method according to claim 10, wherein, in the step (d), an electrical discharge is caused in the bubble and plasma is generated.

13. The liquid treatment method according to claim 10, wherein
a flow path of the water to be treated extends parallel to the longitudinal direction of the dielectric tube, and
the longitudinal axis of the first electrode crosses the flow path of the water to be treated.

14. The liquid treatment apparatus according to claim 1, wherein
the dielectric tube includes a first tube through which the water to be treated flows, and a sub tube perpendicularly connected to the first tube,
the first electrode is at least partially disposed in the sub tube, and
the second electrode is at least partially disposed in the first tube.

15. The liquid treatment method according to claim 10, wherein
the dielectric tube includes a first tube through which the water to be treated flows, and a sub tube perpendicularly connected to the first tube,
the first electrode is at least partially disposed in the sub tube, and
the second electrode is at least partially disposed in the first tube.

* * * * *